United States Patent
Kling

(10) Patent No.: US 6,936,267 B2
(45) Date of Patent: Aug. 30, 2005

(54) ANTI-ACNE COMPOSITIONS AND METHODS OF USE

(76) Inventor: William O. Kling, 4405 Nashwood La., Dallas, TX (US) 75244

(*) Notice: Subject to any disclaimer, the term of this patent is extended or adjusted under 35 U.S.C. 154(b) by 98 days.

(21) Appl. No.: 10/422,596

(22) Filed: Apr. 24, 2003

(65) Prior Publication Data

US 2003/0224064 A1 Dec. 4, 2003

Related U.S. Application Data

(60) Provisional application No. 60/376,043, filed on Apr. 25, 2002.

(51) Int. Cl.$^7$ .................................................. A61K 7/00
(52) U.S. Cl. ........................ 424/401; 514/159; 514/859
(58) Field of Search .......................... 424/401; 514/159, 514/859

(56) References Cited

U.S. PATENT DOCUMENTS

| | | | |
|---|---|---|---|
| 4,507,285 A | 3/1985 | Kühne | 424/530 |
| 4,861,514 A | 8/1989 | Hutchings | 252/187.21 |
| 4,956,184 A | 9/1990 | Kross | 424/661 |
| 6,017,554 A * | 1/2000 | Ratcliff | 424/422 |
| RE37,263 E * | 7/2001 | Kross et al. | 424/661 |
| 6,482,839 B1 * | 11/2002 | Thornfeldt | 514/345 |

FOREIGN PATENT DOCUMENTS

WO PCT/US03/12891 8/2003

\* cited by examiner

*Primary Examiner*—Shelley A. Dodson
*Assistant Examiner*—Konata M. George
(74) *Attorney, Agent, or Firm*—Morgan, Lewis & Bockius, LLP

(57) ABSTRACT

The present invention relates to a composition for the treatment of acne comprising chlorine dioxide or chlorine dioxide generating compounds as acne reduction agents. The invention also relates to a method for treating acne by topically administering one of the compositions in an amount therapeutically effective to reduce the redness and blemishes associated with acne.

4 Claims, No Drawings ions. For example, testosterone stimulates the sebaceous glands accompanying the hair follicles. In response, these glands become enlarged and begin to secrete more sebum than usual. Also, testosterone causes the cells lining a pore to release more keratin, an insoluble protein that is the primary constituent of the hair and the epidermis. Together, the sebum and keratin block a skin pore, resulting in a blackhead. In some instances the blocked pore becomes inflamed resulting in pustules or pimples. This condition is typically known as acne vulgaris. This response is especially prevalent on the face, back, and shoulders, where a greater number of sebaceous glands exist.

ANTI-ACNE COMPOSITIONS AND METHODS OF USE

CROSS REFERENCES TO RELATED APPLICATIONS

This application claims priority to U.S. Provisional Application Ser. No. 60/376,043 filed on Apr. 25, 2002, which is fully incorporated by reference herein.

BACKGROUND OF THE INVENTION

1. Technical Field of the Invention

This invention relates to compositions for treating acne and conditioning the skin cells in patients. The invention further relates to methods of treating acne and conditioning skin cells by administering the compositions to a patient.

2. Description of the Prior Art

The mammalian skin, in particular, human skin, is a multifunctional organ. Not only does the skin provide an external covering to protect the body, but it also performs several specialized functions, such as breathing, perspiring, sensory information processing, and oil production. Oil production, essential to the protective features of the skin, works when an oily substance known as sebum is released from the sebaceous glands, which are large glands located at the base of a hair follicle. This permits the skin to moisturize and waterproof itself, thereby protecting itself from the environment.

Unfortunately, puberty adversely affects the production of sebum, which in some cases is caused by increased levels of testosterone in both males and females. For example, testosterone stimulates the sebaceous glands accompanying the hair follicles. In response, these glands become enlarged and begin to secrete more sebum than usual. Also, testosterone causes the cells lining a pore to release more keratin, an insoluble protein that is the primary constituent of the hair and the epidermis. Together, the sebum and keratin block a skin pore, resulting in a blackhead. In some instances the blocked pore becomes inflamed resulting in pustules or pimples. This condition is typically known as acne vulgaris. This response is especially prevalent on the face, back, and shoulders, where a greater number of sebaceous glands exist.

Acne conglobate, more commonly known as nodular or cystic acne, is a more severe form of acne than acne vulgaris. In the case of nodular acne, the sebum builds up in the gland, mixes with dead cells, and eventually ruptures the follicle wall, which typically forms a deep cyst under the skin. Scarring often results from these deep cysts. Also, acne not only affects a person's appearance, but sometimes has detrimental affects on the person's psychological, social, and occupational status. Present methods of treating acne attempt to address the three separate causes of acne: excess sebum production, keratinization disorders, and increases in the bacteria *Propionibacterium acnes* (*P. acne*).

*P. acne* is a gram-positive, non-spore forming, anaerobic rod bacteria. It is a common resident of the skin's pores and can also live in the oil glands of the human skin. In the pore, it usually resides at the bottom of the pore where the oil duct comes in, because its food source is the sebum or skin oil produced by the oil gland.

The *p. acne* bacteria release lipases to digest the sebum, which has been produced by the oil gland and "delivered" to the pore. The combination of the enzymes and digestive products given off stimulates an intense local inflammation of the cells lining the pore. This inflammation then bursts the hair follicle or pore, especially when the pore opening has been clogged by a mixture of oil and dead skin cells, which has formed a hardened "blackhead."

Once this pore bursts from the inflammation, a cyst may form under the skin, or a lesion may develop on the surface of the skin in the form of a pustule.

Because the *p. acne* bacteria depend upon skin oil or sebum for the food source, it stands to reason that individuals with the highest level of oil production (e.g., teenagers) are commonly the most affected by acne.

Another factor in acne vulgaris is an individual's pore shape, where "v" shaped pores vent oil, skin cell debris and sources of inflammation much more easily than pores which are "pyramid" shaped. With only a small opening at the top, the latter are much more prone to trapping oil, debris and bacteria, which result in inflammation, broken pore walls and lesions. Since not much can be done about the shape of an individual's pores, it is important that any acne treatment focus on removing oil and debris and killing relevant bacteria.

Methods of addressing acne commonly attempt to curb acne by mitigating the effects of sebum through agents such as alcohol, hydrogen peroxide, salicylic acid and benzoyl peroxide. Additionally, antibiotics, applied topically or orally, such as erythromycin or tetracycline are commonly used to control the bacteria. Use of antibiotics leads to overly dry skin, and relapse is common after treatment has ended.

Vitamins and herbs have also been used to treat acne. Vitamin A has proven to be effective in treating acne. Unfortunately, side effects often result from treatment using vitamin A, and patients need to be monitored carefully. Monthly testing of the patient's liver, lipids and glucose is necessary to monitor the response to vitamin A. A popular acne treatment involves the use of isotretinoin (marketed as Accutane®), a retinoid that is related to both retinoic acid and retinol (vitmain A). Also, herbs, such as sassafras and elder flowers, used both individually and in combination have been found to provide effective acne treatment. Additionally, herbs possessing antibiotic properties, such as burdock root and horsetail, may individually aid in the treatment of skin blemishes caused by acne.

Although the above references disclose methods of treating acne, the treatments often involve adverse side effects, such as overdrying of the skin. Furthermore, the above treatments simply address the acne and fail to condition the skin cells to assist in the treatment and to reduce further incidences of acne. Thus, it is desired to find compositions and methods for treating acne by administering the compositions and conditioning the skin to inhibit further acne outbreaks without the adverse side effects present in many conventional acne treatments. The present invention, through a composition comprising chlorine dioxide or chlorine dioxide generating compounds advantageously treats acne without adverse side effects, and conditions skin cells to reduce the likelihood of further acne.

SUMMARY OF THE INVENTION

The present invention relates to a composition for the treatment of acne comprising an acne reduction agent. In an embodiment of the invention, chlorine dioxide or chlorine dioxide generating compounds may be used as acne reduction agents.

The anti-acne compositions of the present invention are useful in reducing the extent of acne vulgaris or acne conglobate on the body of an animal, such as a human. The compositions are administered topically, i.e, on the surface of the area requiring treatment. The administration is preferably to the skin of an animal or human. The preferred application of the compositions is for the treatment of an acne condition on the skin surface. In addition to the treatment of the acne condition and killing of the acne-causing bacteria, the compositions of the present invention also serve to oxidize the treated skin area thereby conditioning the treated skin area and preventing regrowth of the acne-causing bacteria.

The invention also relates to a method for treating acne by topically administering one of the compositions in an amount that is therapeutically effective to reduce the redness and blemishes associated with acne. In addition, the invention relates to a method for conditioning skin cells in a treatment for acne, whereby the skin cells in the treated area are oxidized and debris is removed from the pores.

In another embodiment, the composition is administered in conjunction with at least one additional composition used to treat acne or condition the skin. In a preferred embodiment, the additional composition comprises at least one of alcohol, benzoyl peroxide, resorcinol and its derivatives, salicylic acid, hydrogen peroxide, sulfur erythromycin, clindamycin, tetracycline, isotretinoin, vitamin E, vitamin A and its derivatives, vitamin C, vitamin D, chaparral, dandelion root, licorice root, echinacea, kelp, cayenne, sassafras, elder flowers, pantothenic acid, para-aminobenzoic acid, biotin, choline, inositol, folic acid, calcium, magnesium and potassium.

The compositions of the present invention facilitate the treatment of acne by oxidizing the acne-associated debris which in turn opens the skin pore and permits the compositions to access and destroy the acne-causing bacteria located inside the pore. The compositions of the present invention oxidize the oils present in and around the treatment area, thereby removing the food source of the acne-causing bacteria. The compositions of the present invention inhibit regrowth of the acne-causing bacteria. The acne-treatment compositions of the present invention provide treatment in a manner that does not irritate the skin. In addition, the compositions of the present invention exhibit greater stability relative to prior art compositions.

DETAILED DESCRIPTION OF ILLUSTRATIVE EMBODIMENTS

A composition for treating acne and conditioning the skin cells is disclosed. The composition includes an acne-reducing agent in an amount sufficient to reduce the redness and blemishes associated with acne. In an embodiment, the acne-reducing agent also serves as a skin cell conditioning component in an amount which inhibits or prevents the regrowth of acne. The present composition advantageously treats acne and conditions skin cells with reduced adverse side effects compared to conventional acne compositions and treatment methods. Also, the present invention relates to a method of treating acne using the present composition, alone or in conjunction with other compositions.

The present invention reduces acne in a patient by providing an acne reduction agent comprising chlorine dioxide or at least one chlorine dioxide generating compound. Examples of such chlorine dioxide generating compounds include, but are not limited to, sodium chlorite, sodium chlorate and chlorite ion. The terms "chlorine dioxide generating compound" and "chlorine dioxide compound" are used interchangeably herein. In an embodiment, the acne-reducing component is administered topically.

The acne-reducing agent of the present invention, in addition to treating acne also conditions the skin cells in the treated area. The skin cells are subjected to oxidation, which in addition to conditioning the skin cells (e.g., removal of pore debris), also prevents regrowth of the acne-causing bacteria.

The concentration of the chlorine dioxide compound present in the compositions ranges from about 0.005 to about 0.5 wt %. In an alternate embodiment of the invention, the concentration of the chlorine dioxide composition ranges from about 0.01 to about 0.4 wt %. In yet another embodiment of the invention, the concentration of the chlorine dioxide compound ranges from about 0.03 wt % to 0.15 wt %.

In certain embodiments of the invention, the composition of the present invention comprises at least one of a salicylic acid compound or benzylkonium chloride. As used herein, the term "salicylic acid compound" refers to salicylic acid as well as salts of salicylic acid. In an embodiment of the invention, the amount of salicylic acid in the composition ranges from about 0.3 wt % to 3.0 wt %. In certain embodiments of the invention, the amount of benzylkonium chloride varies from about 0.05 wt % to about 0.15 wt %.

The term "therapeutically effective amount of the composition" refers to the amount of the composition that achieves the desired result, i.e., reduction in the redness of skin and blemishes associated with acne.

In an embodiment of the invention, the anti-acne composition is administered topically.

The invention also relates to a method for treating acne by topically administering one of the compositions in an amount therapeutically effective to reduce the redness and blemishes associated with acne. In addition, the invention relates to a method for conditioning skin cells in a treatment for acne, whereby the skin cells in the treated area are oxidized and debris is removed from the pores.

In another embodiment, the composition is administered in conjunction with at least one additional composition used to treat acne or condition the skin. In a preferred embodiment, the additional composition comprises at least one of alcohol, benzoyl peroxide, resorcinol and its derivatives, salicylic acid, hydrogen peroxide, sulfur erythromycin, clindamycin, tetracycline, isotretinoin, vitamin E, vitamin A and its derivatives, vitamin C, vitamin D, chaparral, dandelion root, licorice root, echinacea, kelp, cayenne, sassafras, elder flowers, pantothenic acid, para-aminobenzoic acid, biotin, choline, inositol, folic acid, calcium, magnesium, potassium and derivatives thereof.

In an embodiment of the invention the composition of the present invention facilitates the treatment of acne by oxidizing the acne-associated debris in and around the area of treatment. The oxidation of the debris opens the skin pore and permits the acne-treatment composition to access and destroy the acne-causing bacteria located at the bottom of the pore. In other embodiments of the invention, the compositions of the present invention oxidize the oils present in and around the treatment area, thereby removing the food source of the acne-causing bacteria. In certain embodiments, the compositions of the present invention further inhibit regrowth of the acne-causing bacteria. The acne-treatment compositions of the present invention provide treatment in a manner that does not irritate the skin. In addition, the compositions of the present invention exhibit greater stability relative to prior art compositions

WORKING EXAMPLES

In certain embodiments of the inventions, the method of reducing acne is carried out as follows. It is to be noted that the treatment regiment discussed below is meant to represent an exemplary embodiment of the invention.

In a first step, the pores are cleaned out with a salicylic acid-based exfoliating cleanser. This helps prevent pores from clogging and provides an open pathway for the medication to reach the *p. acne* bacteria at the bottom of the pore. Next, a composition comprising at least one acne-reducing agent is applied to the pores of the area (skin) requiring treatment. Upon application, the composition kills the *p. acne* bacteria. This composition also reduces or temporarily eliminates the excess oil in the pores. Eliminating the skin oil, or sebum, eliminates the food source for the bacteria, making it difficult for them to reproduce. In addition, the *p. acne* bacteria are anaerobic, which means they thrive in the absence of oxygen. The use of an acne-reducing agent that is also an oxidizing agent discourages regrowth of the acne-causing bacteria.

In a laboratory experiment using over one million CFU (colony-forming units) of *p. acne* bacteria, the anti-acne compositions of the present invention killed 100% of the acne-causing bacteria in under 60 seconds of contact.

Following treatment, a light, oil-free treatment lotion containing salicylic acid is applied to the treated area to remove debris and keep the pores open.

Ingredients

Facial Cleanser

Active Ingredient: Salicylic Acid 2.0%

Other Ingredients: Purified Water, Sodium Laureth Sulfate (and) Lauryl Polyglucose (and) Cocamidopropyl Betaine, SD 40 A Alcohol, Glyceryl Stearate, Glyceryl Strearate & PEG 100 Stearate, Polyethylene, Magnesium Aluminum Silicate, Polyacrylamide (and) $C_{13-14}$ Isoparaffin (and) Laureth-7, Sodium Chlorate, Phenoxyethanol (and) Methylparaben (and) Butylparaben (and) Ethylparaben (and) Propylparaben, Dimethicone Copolyol, Xanthum Gum, Sodium Hydroxide, Disodium EDTA, FD&C Blue #1.

Acne-Treatment Solution

Active Ingredient: Benzylkonium Chloride 0.1%

Other Ingredients: Purified Water, Sodium Chlorate, Lauryl Polyglucose, Dimethicone Copolyol, Disodium EDTA, Sodium Hydroxide, Citric Acid, Sodium Bicarbonate, Sodium Monooleate.

Acne Repair Lotion

Active Ingredient: Salicylic Acid 0.5%

Other Ingredients: Purified Water, Caprylic/Capric Triglyercides, SD 40 A Alcohol, Glyceryl Stearate & PEG 100 Stearate, Glyceryl Stearate, Magnesium Aluminum Silicate, Polyacrylamide (and) $C_{13-14}$ Isoparaffin (and) Laureth-7, Dimethicone, Phenoxyethanol (and) Methylparaben (and) Butylparaben (and) Ethylparaben (and) Propylparaben, Xanthum Gum, Blue-Green Algae Extract, Aloe Vera Gel, Cucumber Extract, Sodium Hydroxide, Disodium EDTA, FD&C Green #3.

The key is to eliminate the *p. acne* bacteria and reduce or eliminate the oil "feedstock" in the pores, or oxidize the environment in the pores to make it inhospitable for *p.acne* growth, without damaging skin cells and overly drying or irritating the skin surface.

The chlorine dioxide compound may be found in a combination of one or more of the items below:

1. A cream or gel containing suspended aluminum oxide or other particles to help open oxidized pores (removing tops of blackheads and white pustules), oxidize the oil and other debris in the pore for easy removal (using proprietary chlorine dioxide compound), and smooth the skin surface.
2. A facial cleanser for cleaning pores which oxidizes the oil for easy removal (via chlorine dioxide compound) and makes the oil "bio-unavailable" to the bacteria as a food source. In addition to the chlorine dioxide compound, the cleanser contains a powerful blend of solubilizers and emulsifiers that keep the skin moistened during treatment.
3. An acne-treatment solution that kills the bacteria within seconds of contact and oxidizes any remaining oil or sebum, making it unavailable to the bacteria as a "food source." Because the *p. acne* bacteria is anaerobic, oxidizing the environment at the bottom of the pore further retards growth of new bacteria.

Because *p. acne* bacteria also reside in the oil glands below the pores, they can regenerate in the pores. However, killing the bacteria inside the pores, removing the oil, and oxidizing the environment delays the regrowth. To further prevent the acne, this process should ideally be repeated at least two times a day.

This system for the treatment of acne is unique because of the penetrating and oxidizing power of the chlorine dioxide compound. The structure of the bacteria is fragile and simple enough that the chlorine dioxide disassembles the bacteria into simpler compounds.

Kill Rate Study 1.0 Objective:

To demonstrate that the test product demonstrates the antimicrobial properties of the label claim.

2.0 References:

2.1 21 CFR 333. Topical antimicrobial drug products for over-the-counter human use.

2.2 Microconsult, Inc. Test Method MC-14. Antiseptic Testing for OTC Drug Products.

3.0 Test Organisms:

Cultures of the following microorganisms are maintained as stock cultures from which working inoculum are prepared. The viable microorganisms used in this test must not be more than five passages removed from the original stock culture. For purposes of the test, one passage is defined as the transfer of organisms from an established culture to fresh medium. All transfers are counted.

3.1 *Propionibacterium acnes* (ATCC No. 11827)

4.0 Materials:

4.1 Test tubes with closures 4.2 Pipettes, 10.0 ml and 1.0 ml serological 4.3 0.85% phosphate buffered saline (PBS) or peptone water, pH 7.0–7.2

4.4 Petri dishes, culture loops and other microbiological apparatus 5.0 Media:

5.1 Tryptic Soy Agar with lecithin and Tween 80

5.2 Sabouraud Dextrose Agar or Potato Dextrose Agar 6.0 Procedure:

6.1 Preparation of Test Samples.

6.1.1 Accurately pipette 9.9 ml of product into an appropriately labeled or coded test tube.

6.1.2 Store test samples at ambient temperature.

6.2 Preparation of inoculum 6.2.1 Inoculate the surface of a suitable volume of solid agar medium from a recently grown stock culture of each of the specified microorganisms. Inoculate the bacterial cultures at 30–35° C. for 4 days under anaerobic conditions.

6.2.2 To harvest the bacterial culture, place a loop full of the test microorganisms from the plate into tube containing sterile PBS and vortex. Adjust the count with sterile saline or additional microorganisms so that the concentration of the inoculum level is between $10^{-6}$ to $10^{-8}$ microorganisms per milliliter of product.

6.2.3 Determine the number of viable microorganisms in each milliliter of the inoculum suspensions by serial dilution in sterile PBS.

6.2.4 Plate dilutions of $10^{-6}$, $10^{-7}$ and $10^{-8}$ for all organisms.

6.2.5 Overlay with approximately 20 ml of 45° C. Tryptic Soy Agar with lecithin and Tween 80 or Sabouraud Dextrose Agar depending on the microorganism being cultured.

6.2.6 Incubate for 48 hours at 30–35° C. for all test organisms.

6.2.7 Calculate the number of organisms as colony forming units per ml (cfu/ml) of inoculum as follows:

$$\frac{Cfu/ml(0.1 \text{ ml})}{9.9 \text{ ml}} = cfu/ml \text{ of product}$$

6.3 Inoculation and Plating of Samples 6.3.1 Aseptically transfer 0.1 ml of each test suspension into the appropriately labeled 9.9 ml sample of test material. Each test organism is inoculated as a pure culture into a single 9.9 ml sample of test material.

6.3.2 Thoroughly mix or stir all samples by vortex.

6.3.3 Let stand for one minute.

6.3.4 Remove aliquots at indicated time and transfer to 9.9 ml saline.

6.3.5 Perform serial dilutions from $10^{-2}$ to $10^{-4}$.

6.3.6 Transfer 1.0 ml of each dilution into a 100×15 mm petri plate in duplicate.

6.3.7 Overlay with approximately 20 ml of 45° C. Tryptic Soy Agar with lecithin and Tween 80.

6.3.8 Gently swirl plates and allow to solidify.

6.3.9 Incubate plates for 48 hours at 35° C. and 48 hours at 25° C.

6.4 Sample Evaluation 6.4.1 Read plates and record results on appropriate data sheet 6.4.2 Using the calculated inoculum concentration of each test microorganism, calculate the log reduction of each microorganism for each kill rate.

7.0 Kill Rate Test:

| One minute Results: | | |
|---|---|---|
| | *P. acnes* ATCC 11827 | |
| Inoculum level | $3.20 \times 10^6$ | |
| Direct | 13 | 2 |
| $10^{-2}$ | 0 | 0 |
| $10^{-4}$ | 0 | 0 |

| -continued | | |
|---|---|---|
| One minute Results: | | |
| | *P. acnes* ATCC 11827 | |
| $10^{-6}$ | NA | NA |
| Average Count | 7.5 | |
| Log Reduction | 5.63 | |

Clinical Study

In a clinical study comprising six test subjects, five of the six subjects who used the acne-reducing compositions of the present invention experienced positive results regarding acne reduction. The average overall reduction in the acne level was 48%, combining pimple count, pimple surface area and redness/inflammation level.

Sensitivity Study

In an independent study, fifty test subjects who participated in a repeat insult patch test showed no skin irritation or sensitivity following repeated application of the acne-reducing compositions of the present invention.

What is claimed is:

1. A composition for the topical treatment of acne which comprises
    a) about 0.005 to about 0.5 wt % of a chlorine dioxide compound,
    b) about 0.3 to about 3.0 wt % of a salicylic acid compound, and
    c) about 0.05 to about 0.15 wt % of benzylkonium chloride.

2. The composition of claim 1 further comprising an additional composition for the treatment of acne.

3. AC The composition of claim 2, wherein said additional composition comprises at least one of alcohol, benzoyl peroxide, resorcinol and its derivatives, salicylic acid, hydrogen peroxide, sulfur erythromycin, clindamycin, tetracycline, isotretinoin, vitamin E, vitamin A and its derivatives, vitamin C, vitamin D, chaparral, dandelion root, licorice root, echinacea, kelp, cayenne, sassafras, elder flowers, pantothenic acid, para-aminobenzoic acid, biotin, choline, inositol, folic acid, calcium, magnesium, potassium and derivatives thereof.

4. A method for the treatment of acne comprising the steps of:
    cleaning a treatment area with a cleanser wherein said cleanser exfoliates the treatment area;
    applying a first composition comprising a chlorine dioxide compound to the treatment area, wherein said first composition eliminates sebum and prevents regrowth of acne-causing bacteria; and
    applying a second composition to the treatment area following treatment, wherein said second composition removes debris from the treatment area.

\* \* \* \* \*